United States Patent
Chung et al.

(10) Patent No.: US 11,179,435 B2
(45) Date of Patent: Nov. 23, 2021

(54) HANGOVER ALLEVIATING COMPOSITION CONTAINING CONJUGATE OF SESAMOL AND PEPTIDE AS ACTIVE INGREDIENT

(71) Applicant: CAREGEN CO., LTD., Anyang-si (KR)

(72) Inventors: Yong Ji Chung, Seoul (KR); Eun Mi Kim, Yongin-si (KR); Eung Ji Lee, Anyang-si (KR)

(73) Assignee: Caregen Co., Ltd., Anyang-si (KR)

( * ) Notice: Subject to any disclaimer, the term of this patent is extended or adjusted under 35 U.S.C. 154(b) by 0 days.

(21) Appl. No.: 16/756,709

(22) PCT Filed: Oct. 16, 2018

(86) PCT No.: PCT/KR2018/012149
§ 371 (c)(1),
(2) Date: Apr. 16, 2020

(87) PCT Pub. No.: WO2019/078570
PCT Pub. Date: Apr. 25, 2019

(65) Prior Publication Data
US 2020/0330546 A1 Oct. 22, 2020

(30) Foreign Application Priority Data
Oct. 16, 2017 (KR) .......................... 10-2017-0133836

(51) Int. Cl.
| | |
|---|---|
| A61K 38/08 | (2019.01) |
| A61K 38/10 | (2006.01) |
| A61K 31/36 | (2006.01) |
| A61K 47/44 | (2017.01) |
| A61K 47/55 | (2017.01) |
| A61K 47/64 | (2017.01) |
| A61P 25/30 | (2006.01) |
| A61P 25/32 | (2006.01) |
| A61P 39/00 | (2006.01) |
| A61P 39/02 | (2006.01) |
| A23L 33/10 | (2016.01) |
| A23L 33/18 | (2016.01) |
| A61K 47/54 | (2017.01) |

(52) U.S. Cl.
CPC .............. *A61K 38/08* (2013.01); *A23L 33/18* (2016.08); *A61K 31/36* (2013.01); *A61K 47/545* (2017.08); *A61K 47/55* (2017.08)

(58) Field of Classification Search
CPC ........ A61K 38/08; A61K 38/10; A61K 31/36; A61K 47/44; A61K 47/545; A61K 47/55; A61K 47/64; A61P 25/30; A61P 25/32; A61P 39/00; A61P 39/02; A23L 33/10; A23L 33/18
See application file for complete search history.

(56) References Cited

U.S. PATENT DOCUMENTS

| | | | |
|---|---|---|---|
| 9,303,064 B2 | 4/2016 | Chung et al. | |
| 2011/0159128 A1 | 6/2011 | Takagaki et al. | |
| 2014/0328782 A1* | 11/2014 | Chung | A61P 9/00 424/62 |
| 2016/0206732 A1* | 7/2016 | Li | A61K 39/001138 |

FOREIGN PATENT DOCUMENTS

| | | |
|---|---|---|
| EP | 2 754 665 A1 | 7/2014 |
| JP | 2005-035997 A | 2/2005 |
| JP | 2014-526459 A | 10/2014 |
| KR | 10-1997-0000236 A | 1/1997 |
| KR | 10-2001-0026440 A | 4/2001 |
| KR | 10-2008-0027429 A | 3/2008 |
| KR | 10-1762136 B1 | 7/2017 |

OTHER PUBLICATIONS

Takagaki et al, Machine English Translation of JP 2005-035997, pp. 1-14. (Year: 2005).*
Kanduc D, "Homology, similarity, and identity in peptide epitope immunodefinition," Journal of Peptide Science, 2012, 18: 487-494. (Year: 2012).*
Pearson WR, "An Introduction to Sequence Similarity ("Homology") Searching," Current Protocols in Bioinformatics, 2013, 3.1.1-3.1.8. (Year: 2013).*
Extended European Search Report for European Patent Application No. 18868191.0 dated Nov. 30, 2020, 27 pages.
Japanese Office Action for Japanese Patent Application No. 2020-520795 dated Mar. 9, 2021, 4 pages.
Cha, B. et al., "Synthesis of Sesamol Derivatives and Biological Activities", Yakhak Hoeji—Journal of the Pharmaceutical Society of Korea, 52(2): 131-136 (Apr. 2008) (English Abstract).
Das, N. et al., "Codrug: An efficient approach for drug optimization", European Journal of Pharmaceutical Sciences, 41(5): 571-588 (Dec. 2010).
Majdalawieh, A. et al., "Seasamol and sesame (Sesamum indicum) oil enhance macrophage cholesterol efflux via up-regulations of PPARγ1 and LXRα transcriptional activity in a MAPK-dependent manner", Eur J Nutr, 54(5): 691-700 (Aug. 2015).
Manon, B. et al.,, "Design, synthesis and evaluation of diclofenac-antioxidant mutual prodrugs as safer NSAIDs", Indian Journal of Chemistry, 48B: 1279-1287 (Sep. 2009).

(Continued)

*Primary Examiner* — Julie Ha
(74) *Attorney, Agent, or Firm* — Merchant & Gould P.C.

(57) ABSTRACT

A hangover alleviating composition comprising a conjugate of sesamol and a peptide as an active ingredient. Specifically, the conjugate of sesamol and a peptide according to the present invention significantly increases the activity of alcohol dehydrogenase (ADH) or aldehyde dehydrogenase (ALDH) involved in the alcohol metabolising process, quickly breaks down the concentration of alcohol in the body, and improves alcohol-induced motor impairment, thus having the advantage of being able to be usefully used as an active ingredient in a hangover alleviating composition.

8 Claims, 4 Drawing Sheets

Specification includes a Sequence Listing.

(56) References Cited

OTHER PUBLICATIONS

Singh, N. et al., "Sesamol loaded solid lipid nanoparticles: a promising intervention for control of carbon tetrachloride induced hepatotoxicity", BMC Conplementary and Alternative Medicine, 15(142): 1-10 (2015).
International Search Report from International Application No. PCT/KR2018/012149, dated May 10, 2019.
Written Opinion from International Application No. PCT/KR2018/012149, dated May 10, 2019.
"The development of drugs for the treatment of liver disease and ethanol intoxification" from *Hovenia dulcis* var. Ministry of Agriculture, Forestry. koreana. Final Research Report. Seoul, Korea, pp. 1-191 (in Korean) (2000), English summary considered only.

\* cited by examiner

HANGOVER ALLEVIATING COMPOSITION CONTAINING CONJUGATE OF SESAMOL AND PEPTIDE AS ACTIVE INGREDIENT

This application is a National Stage Application of International Application No. PCT/KR2018/012149, filed 16 Oct. 2018, which claims benefit of Serial No. 10-2017-0133836, filed 16 Oct. 2017 in the Republic of Korea and which applications are incorporated herein by reference. To the extent appropriate, a claim of priority is made to each of the above disclosed applications.

TECHNICAL FIELD

The present invention relates to a conjugate of sesamol and a peptide, and a hangover alleviating composition containing the conjugate as an active ingredient.

BACKGROUND ART

Alcohol consumption in Korea is the world's highest level, and socio-economic and health hazards from drinking are rapidly increasing. It has been reported that excessive alcohol drinking affects almost all parts of the body, causing many diseases, such as liver disease, gastritis, pancreatitis, high blood pressure, stroke, diabetes, and heart disease.

According to the recent results of the National Health and Nutrition Survey conducted by the Korea Institute for Health and Social Affairs under the Ministry of Health and Welfare, for adults over 20 years old in Korea, the day of drinking is shown to average about 8 days per month, about 11 days for men and 4 days for women. At this time, it has been investigated that the number of inebriation times was found to be approximately 4.7% at least once a week, approximately 10.7% at 1 to 3 times per month, and approximately 13.2% at 1 to 3 times every 3 months, and thus it is quite a concern in terms of national health.

As such, modern people are excessively drinking an excessive amount of alcohol enough not to be controlled in the human body, and the interest in drugs or drinks capable of removing hangover is steadily increasing, and due to these factors, the hangover alleviating drink market has currently grown in a scale exceeding 100 billion won in sales, and has attracted attention even in overseas markets.

Hangover refers to symptoms such as headache, diarrhea, anorexia, nausea, vomiting, chills, and cold sweat that appear after drinking alcohol, and objective symptoms include cognition, decreased motor ability, hematologic changes, and hormonal changes. The cause of hangover is known to be dehydration, toxicity of alcohol and alcohol metabolites (acetaldehyde, formaldehyde, acetone, etc.), and the lack of nutrients (the lack of blood sugar, vitamin, and mineral) caused by malabsorption. The degree of hangover varies greatly depending on the individual's variation according to heredity and environmental conditions (a nutrition status, a motor status, a dehydration degree, and a health condition).

After drinking, alcohol is metabolized through three pathways, in which alcohol is metabolized to acetaldehyde and acetic acid by the action of alcohol dehydrogenase and acetaldehyde dehydrogenase which are present in the gastrointestinal tract or liver when the concentration of ethanol is low, metabolized to acetaldehyde and acetic acid by a microsomal ethanol oxidizing system (MEOS) which is present in the endoplasmic reticulum when the concentration of ethanol is high, and then finally decomposed into carbon dioxide ($CO_2$) and water ($H_2O$) through the action of catalase which is present in the peroxisome. When a proper amount of alcohol is introduced, the above-described metabolic system smoothly acts, so that the symptoms caused by alcohol do not occur, but when a large amount of alcohol is introduced, the balance of the metabolic system is destroyed and bio-homeostasis is not maintained, and as a result, headache or heavy head feelings, the loss of concentration, heartburn, and indigestion may be caused in a short term and liver dysfunction may occur in a long term.

Meanwhile, currently, hangover relieving drinks containing astragalus, lotus seed, rice germ and hovenia extracts, hangover relieving drinks containing a fermented rice-soybean extract and milk thistle extract powder as a main ingredient, and hangover relieving drinks containing alder tree and rowan extracts as an active ingredient are commercially available, but since most of these drinks contain the extracts as the active ingredients, the securing of raw materials is flexible, and it is expensive to construct processes or equipment required for extraction for mass production. In addition, there are a variety of problems in that due to the nature of the extracts, there is a significant difference in the degree of relieving hangover depending on an individual, and a long time is required for relieving hangover. For this reason, it is still necessary to develop a product that is easy and efficient in the securing of raw materials or mass-production, and can simultaneously solve alcohol degradation and hangover relief in a short time.

DISCLOSURE

Technical Problem

An object of the present invention is to provide a conjugate of sesamol and a peptide for relieving hangover.

Another object of the present invention is to provide a hangover relieving composition comprising the conjugate as an active ingredient.

Yet another object of the present invention is to provide a hangover relieving method comprising administering the conjugate or the composition comprising the conjugate as an active ingredient to a subject in need thereof.

Technical Solution

In order to achieve the above objects, an aspect of the present invention provides a pharmaceutical composition for preventing or relieving hangover comprising a conjugate of sesamol and a peptide as an active ingredient.

Another aspect of the present invention provides a health food for preventing or relieving hangover comprising a conjugate of sesamol and a peptide as an active ingredient.

Yet another aspect of the present invention provides a method for preventing or relieving hangover comprising administering a conjugate of sesamol and a peptide or a composition comprising the conjugate as an active ingredient to a subject in need thereof.

Advantageous Effects

According to the present invention, the conjugate of sesamol and the peptide has advantages of improving significantly the activity of alcohol dehydrogenase (ADH) and aldehyde dehydrogenase (ALDH) involved in an alcohol degradation process, rapidly degrading alcohol in the body, and improving alcohol-induced motor impairment, thereby being able to be usefully used as an active ingredient in the hangover relieving composition.

However, the effects of the present invention are not limited to the above-mentioned effects, and other effects not mentioned will be clearly understood by those skilled in the art from the following description.

DESCRIPTION OF DRAWINGS

FIG. 3 is a diagram illustrating a result of confirming an effect of increasing mRNA expression of alcohol dehydrogenase (ADH) and ALDH with respect to a conjugate of sesamol and a peptide having an amino acid sequence of SEQ ID NO: 1 (FIG. 3A) and a conjugate of sesamol and a peptide having an amino acid sequence of SEQ ID NO: 2 (FIG. 3B).

FIG. 6 is a graph showing a result of confirming a hangover relieving effect of a conjugate complex mixed with a conjugate of sesamol and a peptide according to the present invention after 1 hour of alcohol intake (FIG. 6A) and after 2 bours of alcohol intake (FIG. 6B).

In FIGS. 1 to 3, 'SEQ ID NO: 1' is a group treated with a conjugate of sesamol and a peptide having an amino acid sequence of SEQ ID NO: 1 and 'SEQ ID NO: 2' is a group treated with a conjugate of sesamol and a peptide having an amino acid sequence of SEQ ID NO: 2. In FIGS. 4 to 6, the 'conjugate complex' is a group treated with a complex mixed with the conjugate of the sesamol and the peptide having an amino acid sequence of SEQ ID NO: 1 and the conjugate of the sesamol and the peptide having an amino acid sequence of SEQ ID NO: 2 at a weight ratio of 1:1.

BEST MODE

Hereinafter, the present invention will be described in detail.

1. Pharmaceutical Composition for Preventing or Relieving Hangover

An aspect of the present invention provides a pharmaceutical composition for preventing or relieving hangover comprising a conjugate of sesamol and a peptide as an active ingredient.

The sesamol represents a compound of Chemical Formula of $C_7H_6O_3$, and has a chemical structure of the following Chemical Formula 1.

The peptide refers to a polymer consisting of two or more amino acids linked by peptide bonds, and has a disadvantage that the peptide is not effectively introduced to a target tissue or cell due to a too large size of the peptide itself, or the peptide disappears in the body in a short time due to a short half-life. Accordingly, the peptide of the present invention comprises 20 or less, preferably 15 or less, more preferably 10 or less amino acids.

The peptide of the present invention may include an amino acid sequence of SEQ ID NO: 1 or SEQ ID NO: 2 and may be variants or fragments of amino acids having different sequences by deletion, insertion, and substitution of amino acid residues or combinations thereof within a range that does not affect the hangover relief of the present invention. Amino acid exchange at a peptide level that does not change the hangover relieving activity of the peptide as a whole has been known in the art. In some cases, the amino acid exchange may be modified by phosphorylation, sulfation, acrylation, glycosylation, methylation, farnesylation, and the like. Accordingly, the present invention includes a peptide having an amino acid sequence substantially identical to the peptide having the amino acid sequence of SEQ ID NO: 1 or SEQ ID NO: 2, and variants or active fragments thereof. The substantially identical peptide refers to an amino acid sequence having sequence homology of 75% or more, preferably 80% or more, more preferably 90% or more, and most preferably 95% or more with the amino acid sequence of SEQ ID NO: 1 or SEQ ID NO: 2, respectively. In addition, the peptide may further include an amino acid sequence prepared for a specific purpose to increase a targeting sequence, a tag, labeled residues, half-life or peptide stability.

Further, the peptide of the present invention may be obtained by various methods well-known in the art. As an example, the peptide may be prepared by using polynucleotide recombination and a protein expression system or prepared by an in-vitro synthesis method through chemical synthesis such as peptide synthesis, a cell-free protein synthesis method, and the like.

In addition, in order to obtain better chemical stability, enhanced pharmacological properties (half-life, absorbency, titer, efficacy, etc.), modified specificity (e.g., a wide biological activity spectrum), and reduced antigenicity, an N-terminus of the peptide is bound to a protective group selected from the group consisting of an acetyl group, a fluorenyl methoxy carbonyl group, a formyl group, a palmitoyl group, a myristyl group, a stearyl group, and polyethylene glycol (PEG) to improve the stability. Meanwhile, the 'stability' means storage stability (e.g., room-temperature storage stability) as well as in-vivo stability that protects the peptide of the present invention from the attack of a protein cleavage enzyme in vivo.

The sesamol and the peptide may be linked to each other by a linker. The linker may be aliphatic, alicyclic or aromatic dicarboxylic acid, preferably aliphatic or alicyclic dicarboxylic acid, and more preferably aliphatic dicarboxylic acid. More specifically, the aliphatic dicarboxylic acid may be dicarboxylic acid having a chemical structure of Chemical Formula 2 below.

[Chemical Formula 1]

[Chemical Formula 2]

In Chemical Formula 2, R may be an alkylene group having 1 to 12 carbon atoms, preferably 1 to 10 carbon atoms, and more preferably 1 to 6 carbon atoms; an alkenylene group having 2 to 12 carbon atoms, preferably 2 to 10 carbon atoms, and more preferably 2 to 6 carbon atoms; or an alkynylene group having 2 to 12 carbon atoms, preferably 2 to 10 carbon atoms, and more preferably 2 to 6 carbon atoms.

In particular, the linker may be an aliphatic saturated dicarboxylic acid having a chemical structure of Chemical Formula 3 below.

[Chemical Formula 3]

In Chemical Formula 3, n is an integer of 1 to 12, preferably 1 to 10, more preferably 1 to 6, and most preferably 1 to 4.

A carboxyl group on one side of the dicarboxylic acid forms an ester bond with A hydroxy group (—OH) of the sesamol, and a carboxyl group on the other side of the dicarboxylic acid forms a peptide bond with an amino group (—NH$_2$) exposed to the N-terminus of the peptide, so that the sesamol and the peptide are linked to each other to form the conjugate of the present invention.

Further, the conjugate of the sesamol and the peptide of the present invention may be prepared by i) preparing the peptide, ii) binding a linker to the peptide by reacting the linker with the peptide, and iii) binding the sesamol to the linker by reacting the sesamol with the linker bound to the peptide.

In addition, the conjugate of the sesamol and the peptide may be a conjugate of sesamol and a peptide comprising an amino acid sequence of SEQ ID NO: 1, a conjugate of sesamol and a peptide comprising the amino acid sequence of SEQ ID NO: 2, or mixtures thereof.

In order to confirm the effect of increasing the activity of aldehyde dehydrogenase (ALDH) by the conjugate of the sesamol and the peptide of the present invention, in a specific embodiment of the present invention, liver carcinoma cells are treated with the conjugate of the sesamol and the peptide having the amino acid sequence of SEQ ID NO: 1 or SEQ ID NO: 2, respectively, and then the ALDH activity assay is performed. As a result, it was confirmed that the ALDH activity increased in a concentration-dependent manner in the cells treated with the conjugate of the sesamol and the peptide of the present invention (see FIGS. 1 and 2).

In addition, in order to confirm an effect of increasing the expression of alcohol dehydrogenase (ADH) and ALDH involved in an alcohol degradation process of the conjugate of the sesamol and the peptide of the present invention, in a specific embodiment of the present invention, liver carcinoma cells are treated with the conjugate of the sesamol and the peptide having the amino acid sequence of SEQ ID NO: 1 or SEQ ID NO: 2, respectively, and then the expression levels of ADH and ALDH were confirmed through RT-PCR. As a result, it was confirmed that the mRNA expression of ADH4, ALDH1, and ALDH2 is significantly increased in the cells treated with the conjugate of the sesamol and the peptide of the present invention as compared with an untreated control group (see FIG. 3).

In addition, in order to confirm an effect of improving the motor ability of the conjugate of the sesamol and the peptide of the present invention, in a specific embodiment of the present invention, the conjugate of the sesamol and the peptide having the amino acid sequence of SEQ ID NO: 1 or SEQ ID NO: 2 is mixed at a weight ratio of 1:1 and then administered to a mouse model with alcohol, and thereafter, a behavioral test was performed. As a result, it was confirmed that the group administered with the conjugate complex significantly improved the motor ability decreased by alcohol intake (see FIG. 4).

Further, in order to confirm an alcohol degradation effect of the conjugate of the sesamol and the peptide of the present invention, in a specific embodiment of the present invention, the conjugate complex was administered to the mouse model with alcohol and then the aldehyde assay in the mouse serum was performed. As a result, it was confirmed that the group administered with the conjugate complex significantly reduced the aldehyde concentration in the serum (see FIG. 5).

Furthermore, in order to confirm a hangover relieving effect of the conjugate of the sesamol and the peptide of the present invention, in a specific embodiment of the present invention, clinical trial subjects were subjected to take the conjugate complex with alcohol, and then a blood alcohol concentration was measured after 1 hour and 2 hours. As a result, it was confirmed that the e group administered with the conjugate complex significantly reduced the blood alcohol concentration (see FIG. 6).

Accordingly, the conjugate of the sesamol and the peptide of the present invention significantly increases the activity of alcohol dehydrogenase or aldehyde dehydrogenase involved in the alcohol degradation process, rapidly degrades the alcohol concentration in the body, and improves the alcohol-induced motor impairment, thereby being able to be usefully used as an active ingredient in the hangover relieving composition.

Meanwhile, the conjugates of the sesamol and the peptides of the present invention may be carried in pharmaceutically acceptable carriers, such as colloidal suspensions, powders, saline, lipids, liposomes, microspheres, or nano spherical particles. These conjugates may form or be related to a complex with a vehicle and may be carried in vivo by using carrying systems known in the art, such as lipids, liposomes, microparticles, gold, nanoparticles, polymers, condensation reagents, polysaccharides, polyamino acids, dendrimers, saponin, adsorption enhancing substances or fatty acids.

Besides, the pharmaceutically acceptable carrier may include lactose, dextrose, sucrose, sorbitol, mannitol, starch, acacia Gum, calcium phosphate, alginate, gelatin, calcium silicate, microcrystalline cellulose, polyvinylpyrrolidone, cellulose, water, syrup, methylcellulose, methylhydroxybenzoate, propylhydroxybenzoate, talc, magnesium stearate, and mineral oil, which are generally used in preparation, but is not limited thereto. Further, the pharmaceutical composition may further include a lubricant, a wetting agent, a sweetening agent, a flavoring agent, an emulsifying agent, a suspending agent, a preservative, and the like, in addition to the above ingredients.

The pharmaceutical composition of the present invention may be administered orally or parenterally (e.g., applied intramuscularly, intravenously, intraperitoneally, subcutaneously, intradermally, or topically) according to a desired method, and a dose varies depending on the condition and weight of a patient, a degree of disease, a drug form, and route and time of administration, but may be appropriately selected by those skilled in the art.

The pharmaceutical composition of the present invention is administered in a pharmaceutically effective dose. In the present invention, the 'pharmaceutically effective dose' refers to a sufficient amount to treat diseases at a reasonable benefit/risk ratio applicable to medical treatment, and an effective dose level may be determined according to factors including the type and severity of disease of a patient, the activity of a drug, the sensitivity to a drug, a time of administration, a route of administration, an emission rate, a duration of treatment, and simultaneously used drugs, and other factors well-known in the medical field. The pharmaceutical composition according to the present invention may be administered as a separate therapeutic agent or in combination with other hangover relieving agents, and may be administered simultaneously, separately, or sequentially with or from conventional hangover relieving agents, and may be administered singly or multiply. It is important to administer an amount capable of obtaining a maximum effect with a minimal amount without side-effects by considering all the factors and this may be easily determined by those skilled in the art.

Specifically, the effective dose of the pharmaceutical composition of the present invention may vary depending on the age, sex, condition, and weight of a patient, the absorbance of an active ingredient in vivo, an inactivation rate, an excretion rate, a disease type, and drugs to be used in combination, and may be increased or decreased according to a route of administration, the severity of obesity, sex, weight, age, and the like. For example, the peptide of the present invention may be administered at about 0.0001 μg to 500 mg, preferably 0.01 μg to 100 mg per 1 kg of patient's body weight per day.

2. Health Food for Preventing or Relieving Hangover

Another aspect of the present invention provides a health food for preventing or relieving hangover comprising a conjugate of sesamol and a peptide as an active ingredient. The conjugate of the sesamol and the peptide is the same as the conjugate of the sesamol and the peptide described in the section '1. Pharmaceutical composition for preventing or relieving hangover', and thus, for the detailed description, the section '1. Pharmaceutical composition for preventing or relieving hangover' is used, and hereinafter, only a specific configuration of the health food will be described.

Like the pharmaceutical composition, the conjugate of the sesamol and the peptide of the present invention significantly increases the activity of alcohol dehydrogenase or aldehyde dehydrogenase involved in the alcohol degradation process, rapidly degrades the alcohol concentration in the body, and improves the alcohol-induced motor impairment, thereby being able to be usefully used as an active ingredient in the health food for relieving the hangover.

In the health food of the present invention, the active ingredient may be added to the food as it is or used with other foods or food ingredients, and may be appropriately used according to a general method. The mixing amount of the active ingredients may be suitably determined according to the purpose of use thereof (for prevention or improvement). In general, in preparation of foods or drinks, the composition of the present invention may be added in an amount of preferably 15 wt % or less, more preferably 10 wt % or less with respect to raw materials. However, in the case of long-term intake for the purpose of health and hygiene or health regulation, the amount may be equal to or lower than the above range.

The health food of the present invention may contain other ingredients as essential ingredients without particular limitation, in addition to the active ingredients. For example, like general drinks, various flavoring agents or natural carbohydrates may be contained as an additional ingredient. Examples of the above-mentioned natural carbohydrates may include general sugars, such as monosaccharides such as glucose, fructose, and the like; disaccharides such as maltose, sucrose, and the like; and polysaccharides such as dextrin, cyclodextrin, and the like, and sugar alcohols such as xylitol, sorbitol, erythritol, and the like. As flavoring agents other than those described above, natural flavoring agents (thaumatin, stevia extract (e.g., rebaudioside A, glycyrginine, etc.)) and synthetic flavoring agents (saccharin, aspartame, etc.) may be advantageously used. The ratio of the natural carbohydrates may be appropriately determined by the selection of those skilled in the art.

In addition, the health food of the present invention may contain various nutrients, vitamins, minerals (electrolytes), flavoring agents such as synthetic and natural flavoring agents, coloring agents and enhancers (cheese, chocolate, etc.), pectic acid and salts thereof, alginic acid and salts thereof, organic acid, a protective colloidal thickener, a pH adjusting agent, a stabilizer, a preservative, glycerin, alcohol, a carbonic acid agent used in a carbonated drink, and the like. These ingredients may be used independently or in combination, and the ratio of these additives may also be appropriately selected by those skilled in the art.

3. Method for Preventing or Relieving Hangover

Yet another aspect of the present invention provides a method for preventing or relieving hangover comprising administering a conjugate of sesamol and a peptide or a composition comprising the conjugate as an active ingredient to a subject in need thereof.

The conjugate of the sesamol and the peptide is the same as the conjugate of the sesamol and the peptide described in the section '1. Pharmaceutical composition for preventing or relieving hangover', and thus, for the detailed description, the section '1. Pharmaceutical composition for preventing or relieving hangover' is used.

As described above, the conjugate of the sesamol and the peptide of the present invention or the composition comprising the conjugate as an active ingredient, for example, the pharmaceutical composition or the health food may rapidly degrade alcohol in the body and improve the alcohol-induced motor impairment, thereby achieving the excellent hangover relieving effect when administering the conjugate or the composition to the subject, for example, human in need thereof.

Hereinafter, the present invention will be described in detail by Preparation Examples and Experimental Examples.

However, the following Preparation Examples and Experimental Examples are just illustrative of the present invention, and the contents of the present invention are not limited to the following Preparation Examples and Experimental Examples.

[Preparation Example 1] Preparation of Succinylated Peptide

A peptide having an amino acid sequence of SEQ ID NO: 1 and a peptide having an amino acid sequence of SEQ ID NO: 2 described in the following Table 1 were synthesized by using an automatic peptide synthesizer (Milligen 9050, Millipore, USA), respectively, and each peptide (1 mmol) and succinic anhydride (200 mg, 2.0 equiv.) were dissolved in N,N-dimethylformamide (DMF, 10 ml) and added with N,N-diisopropylethylamine (DIEA) (388 mg, 3.0 equiv.), and reacted at room temperature for 2 hours to succinylate each peptide. These synthesized succinylated peptides were separately purified using C18 reversed-phase high-performance liquid chromatography (HPLC) (Waters Associates, USA). The column used ACQUITY UPLC BEH300 C18 (2.1 100 mm, 1.7 um, Waters Co, USA).

TABLE 1

| Sequence No. | Amino acid sequence |
|---|---|
| 1 | SIPCKLQSG |
| 2 | WLNRRAN |

[Preparation Example 2] Preparation of Conjugate of Sesamol and Peptide of the Present Invention In a peptide reactor, the succinylated peptide (1 mmol) prepared in [Preparation Example 1] was dissolved in dimethylformamide (DMF, 10 ml), added with 1-hydroxybenzotriazole (HOBt, 270 mg, 2.0 equiv.), (benzotriazole-1-yloxy)tripyrrolidinophosphonium hexafluorophosphate (PyBOP, 1.04 g, 2.0 equiv.), and sesamol (277 mg, 2.0 equiv.), and stirred for 30 minutes. The mixture was added with N,N-diisopropylethylamine (DIEA, 388 mg, 3 equiv.) and reacted for 4 hours at room temperature, and then subjected to recrystallization, filtration, and drying processes using diethyl ether (10 ml, 10 mmol) to obtain a conjugate of sesamol and a peptide having an amino acid sequence of SEQ ID NO: 1 and a conjugate of sesamol and a peptide having an amino acid sequence of SEQ ID NO: 2, respectively.

[Experimental Example 1] Confirmation of Effect of Increasing Activity of Aldehyde Dehydrogenase Alcohol was converted to acetaldehyde by alcohol dehydrogenase (ADH), an alcohol degrading enzyme, and the converted acetaldehyde was converted and degraded to acetate by aldehyde dehydrogenase (ALDH). Therefore, in order to confirm the effect of increasing the activity of ALDH involved in the alcohol degradation process, liver carcinoma cells were treated with the two types of conjugates of the sesamol and the peptides prepared in [Preparation Example 2], respectively, and then the ALDH activity assay was performed.

Specifically, liver hepatocellular carcinoma (HepG2) cells, which were human liver carcinoma cells, were inoculated into a 6-well plate at a density of $4 \times 10^5$ cells/well and then incubated overnight. Thereafter, the two types of conjugates of the sesamol and the peptides prepared in [Preparation Example 2] were treated at a concentration of 50 μM or 100 μM, respectively, and incubated for 24 hours, and the cells were collected and then the ALDH activity was analyzed using an ALDH activity assay kit (abcam, ab155893). Meanwhile, a positive control group was treated with 5 μM sulfolaphane.

For the ALDH activity assay, each of the collected cells was treated with an ALDH activity assay buffer included in the kit, and then lysed with a homogenizer under ice. Thereafter, the cells were centrifuged under a condition of 4° C. and 13,000 rpm for 10 minutes and then a supernatant was collected. The collected supernatant was treated with an ALDH assay buffer, an ALDH substrate, and acetaldehyde and reacted at room temperature for 1 hour, and the absorbance was measured at 450 nm for 20 minutes at intervals of 2 minutes using a spectrophotometer. Thereafter, the ALDH activity was calculated using the following [Equation 1].

$$ALDH \text{ activity} = \frac{B}{\Delta T \times V} \times \text{Dilution magnification} = nmol/min/ml = mU/ml \quad \text{[Equation 1]}$$

Figure 1:
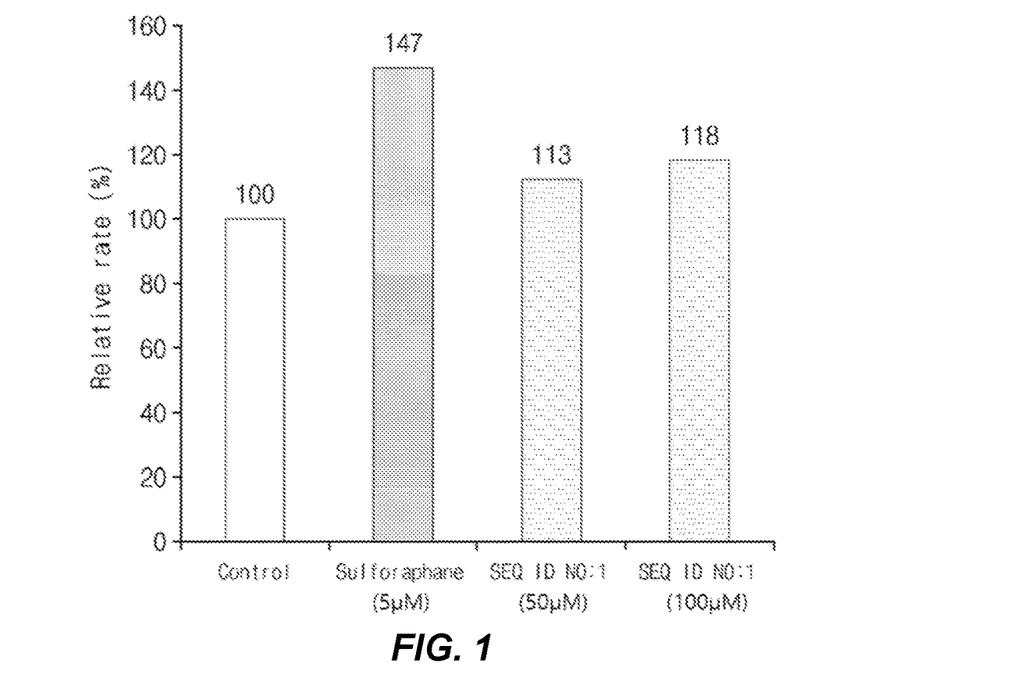
FIG. 1 is a graph showing a result of confirming an effect of increasing the activity of aldehyde dehydrogenase (ALDH) by a conjugate of sesamol and a peptide having an amino acid sequence of SEQ ID NO: 1.
Figure 2:
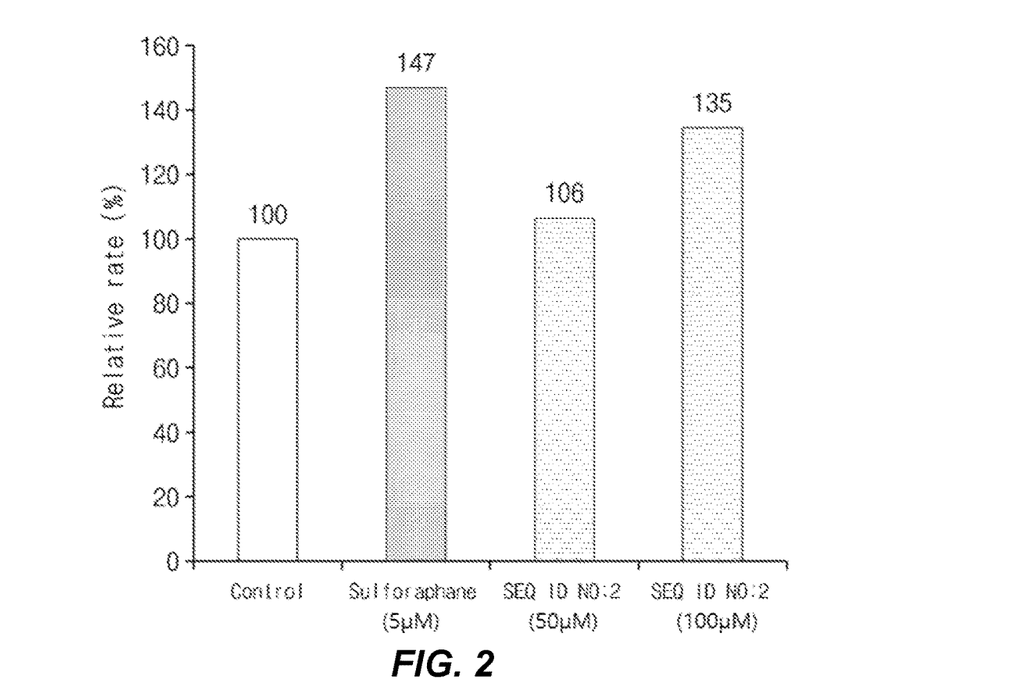
FIG. 2 is a graph showing a result of confirming an effect of increasing the activity of aldehyde dehydrogenase (ALDH) by a conjugate of sesamol and a peptide having an amino acid sequence of SEQ ID NO: 2.

B: NADH amount (nmol) generated in experimental group
$\Delta T$: reaction time (min)
V: volume (ml) of experimental group used in reaction well As a result, as illustrated in FIGS. 1 and 2, it was confirmed that the two types of conjugates of the sesamol and the peptides of the present invention significantly increased the ALDH activity compared to an untreated control group, respectively (FIGS. 1 and 2).

[Experimental Example 2] Confirmation of Effect of Increasing Expression of ADH and ALDH In order to confirm an effect of increasing the expression of ADH and ALDH involved in the alcohol degradation process, liver carcinoma cells were treated with the two types of conjugates of the sesamol and the peptides prepared in [Preparation Example 2], respectively, and then RT-PCR was performed.

Specifically, HepG2 cells were inoculated in a 6-well plate at a density of $4 \times 10^5$ cells/well, and then incubated overnight. Thereafter, the two types of conjugates of the sesamol and the peptides prepared in [Preparation Example 2] were treated at a concentration of 10 μM or 50 μM, respectively, and incubated for 6 hours, and the cells were collected. Thereafter, the total RNA was isolated from the collected cells according to a manufacturer's protocol using Trizol (Invitrogen, USA), and then 1 μg of the isolated RNA was synthesized to cDNA according to a manufacturer's protocol using a cDNA synthesis kit (Intron, Korea). The cDNA was subjected to PCR using primers shown in Table 2 below, and then electrophoresed on a 5% agarose gel to confirm mRNA expression levels of ADH4, ALDH1, and ALDH2.

TABLE 2

| Primer | | Sequence (5'→3') | Sequence No. |
|---|---|---|---|
| ADH4 | Forward | CTGAAACCATGAAAGCAGCC | 3 |
| | Backward | GCCGATTATTAGCTCCTCTGG | 4 |
| ALDH1 | Forward | GGAGCCAAAAGGGTCATCAT | 5 |
| | Backward | GTGATGGCATGGACTGTGGT | 6 |
| ALDH2 | Forward | CAAATTACAGGGTCAACTGCTAT | 7 |
| | Backward | CCACACTCACAGTTTTCACTTC | 8 |

Figure 3A:
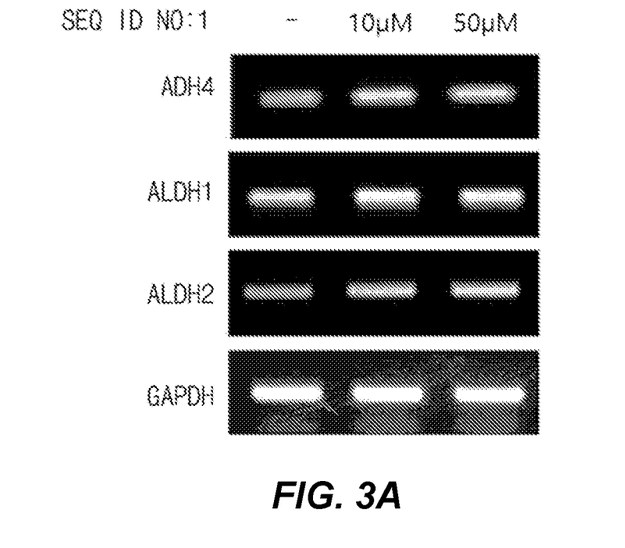
Figure 3B:
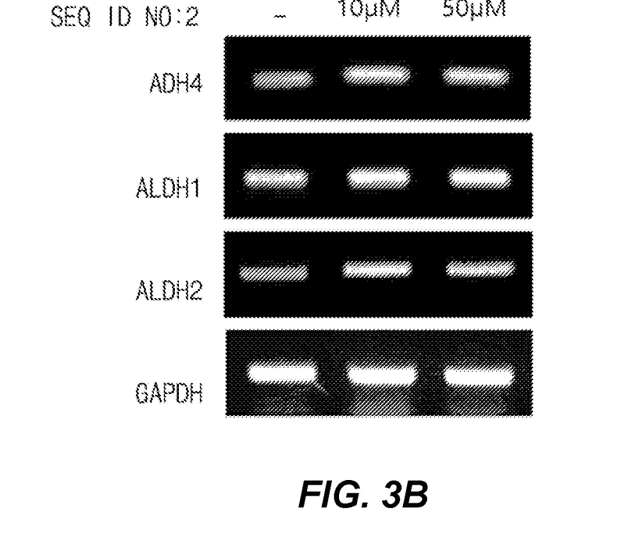

As a result, as illustrated in FIG. 3, it was confirmed that the two types of conjugates of the sesamol and the peptides of the present invention significantly increased the mRNA expression of ADH4, ALDH1, and ALDH2 as compared with an unrelated control group, respectively (see FIG. 3). For rapid alcohol degradation, it is required to induce rapid degradation by increasing the activities of ADH and ALDH, which are enzymes involved in alcohol degradation, and thus, from the results of [Experimental Example 1] and

[Experimental Example 2], it can be seen that the conjugates of the sesamol and the peptides of the present invention significantly increase the activities and expression of ADH and ALDH to induce rapid degradation of alcohol.

[Experimental Example 3] Confirmation of Effect of Improving Motor Ability on Alcohol-Administered Mouse Model In order to confirm the effect of improving the motor ability in an animal model administered with alcohol, after the conjugate of the sesamol and the peptide prepared in [Preparation Example 2] and alcohol were administered to the mouse model and then a behavior test was performed using a Rota-rod device.

Specifically, 8-week-old male Balb/c mice were used as a mouse model and pre-bred for 1 week by freely feeding solid feed and tap water and then used for the test. In addition, the mice were divided into ① a normal control group, ② an alcohol administered group, and ③ an experimental group, and 5 mice per group were used for the test.

For the behavioral test, the mice were placed on a Rota-rod device and subjected to adaptive training three or more times.

Before the behavioral test was performed, the mice maintained on an empty stomach for 4 hours, placed on a Rota-rod device before alcohol administration, walked in a condition where the rpm gradually increased from 4 rpm to 40 rpm, then lost the motor ability, and the time taken to fall down to the bottom stool was measured and converted into second units to obtain a latency to fall (sec.) value.

Thereafter, the conjugate of the sesamol and the peptide having the amino acid sequence of SEQ ID NO: 1 and the conjugate of the sesamol and the peptide having the amino acid sequence of SEQ ID NO: 2 were mixed at a weight ratio of 1:1 to prepare a complex (hereinafter, referred to as a 'conjugate complex') and then the complex was dissolved in water and administered orally to mice in an experimental group at a dose of 100 mg/kg and then left for 30 minutes. Meanwhile, in the case of the normal control group, the same volume of water was orally administered. Subsequently, 20% alcohol was orally administered to individual mice in the alcohol-administered group and the experimental group at 400 µl per individual, and after 30 minutes, 1 hour, and 2 hours, latency to fall (sec.) values were obtained for each group using a Rota-rod device in the same manner as described above.

Figure 4:
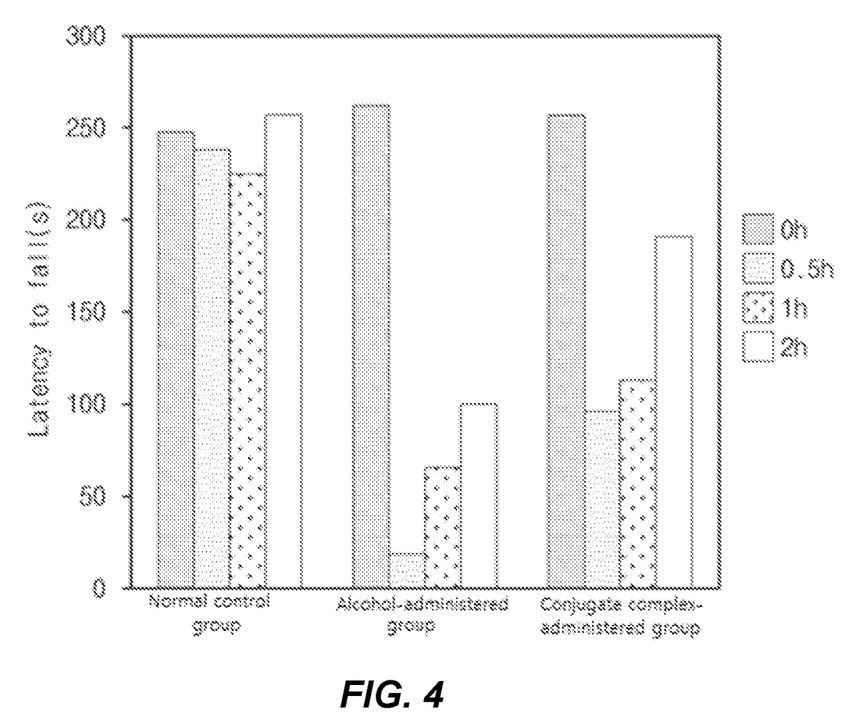
FIG. 4 is a graph showing a result of confirming an effect of improving the motor ability of a mouse model by a conjugate complex mixed with a conjugate of sesamol and a peptide according to the present invention.

As a result, as illustrated in FIG. 4, before the behavioral test was performed, the normal control group, the alcohol-administered group, and the experimental group all had an average latency to fall (sec.) value of about 250, and all the three groups had similar latency to fall (sec.) values.

On the other hand, as a result of performing the behavior test after 30 minutes, 1 hour, and 2 hours of administration of alcohol, it was confirmed that the alcohol-administered group significantly reduced the latency to fall (sec.) value, while the experimental group administered with the conjugate complex of the present invention together with alcohol significantly increased the latency to fall (sec.) value compared to the alcohol-administered group (FIG. 4).

From the above results, it can be seen that the conjugates of the sesamol and the peptides of the present invention significantly improve the motor ability decreased by alcohol intake.

[Experimental Example 4] Confirmation of Alcohol Degrading Effect on Alcohol-Administered Mouse Model In order to confirm an alcohol degrading effect in an animal model administered with alcohol, aldehyde assay in the mouse serum was performed.

Specifically, the bloods in ① the normal control group, ② the alcohol-administered group, and ③ the experimental group after completing the behavior test for 2 hours in the [Experimental Example 3] were extracted, respectively. Then, the extracted blood was hardened at room temperature for 20 minutes, and then centrifuged at 3,000 rpm to obtain the serum as a supernatant. The aldehyde assay in the obtained serum was performed using an aldehyde quantification assay kit (abcam, ab112113). More specifically, a 2×Yellos reaction mixture of the obtained serum and the kit was mixed at 1:1 and then reacted at room temperature for 1 hour, and thereafter, the absorbance was measured at 550 nm using a spectrophotometer.

Figure 5:
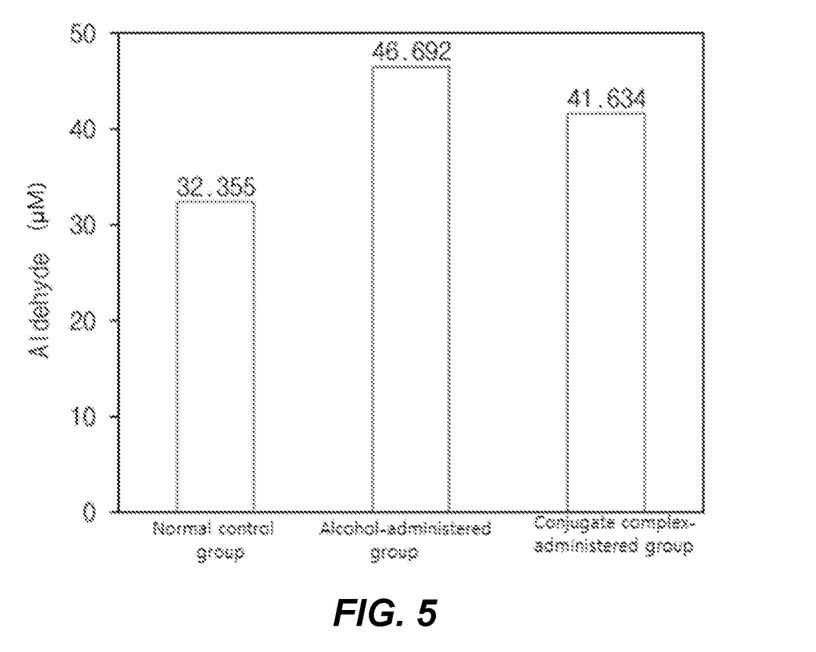
FIG. 5 is a graph showing a result of confirming an effect of reducing an aldehyde concentration in the serum of a mouse model by a conjugate complex mixed with a conjugate of sesamol and a peptide according to the present invention.

As a result, as illustrated in FIG. 5, it was confirmed that the alcohol-administered group had a higher aldehyde concentration in the serum than that in the normal control group, whereas the experimental group administered with the conjugate complex of the present invention together with alcohol had a significantly lower aldehyde concentration in the serum than that in the alcohol-administered group (FIG. 5).

From the above results, it can be seen that the conjugates of the sesamol and the peptides of the present invention significantly increase the activities and expression of ADH and ALDH to induce rapid degradation of alcohol.

[Experimental Example 5] Confirmation of Hangover Relieving Effect

In order to confirm a hangover relieving effect, clinical trials were conducted using the conjugate complex.

Specifically, 4 adult men and 4 adult women aged 20 to 40 were recruited to conduct the clinical trials. Thereafter, a control test was performed to examine a basic alcohol absorption pattern for the subjects. More specifically, after eating the same meal, the subjects maintained on an empty stomach for 3 hours and drunk a commercial 20% liquor (soju) bottle for 30 minutes. Blood alcohol concentrations after 1 hour and 2 hours of drinking were measured using a breathalyzer (Sentek Korea, AL-9000).

Thereafter, in order to confirm the hangover relieving effect of the conjugate complex, after 3 days of the control test, 100 ml of a drink containing 100 ppm of each of the two types of conjugates of the sesamol and the peptides prepared in [Preparation Example 2] was taken to the same subject, and after 30 minutes, alcohol was taken in the same manner as the method described above and the blood alcohol concentration was measured, and then the blood alcohol concentrations were compared with the control test result and analyzed to be graphed.

Figure 6A:
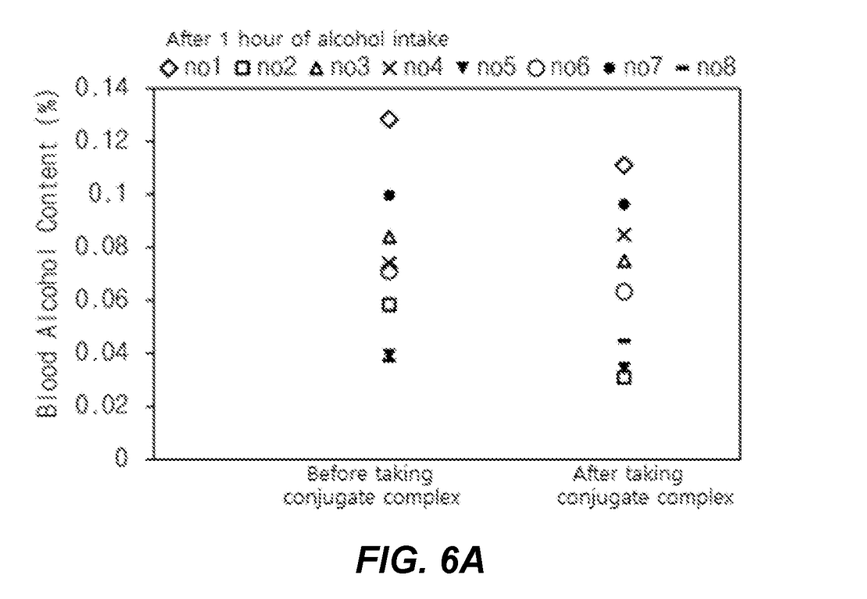
Figure 6B:
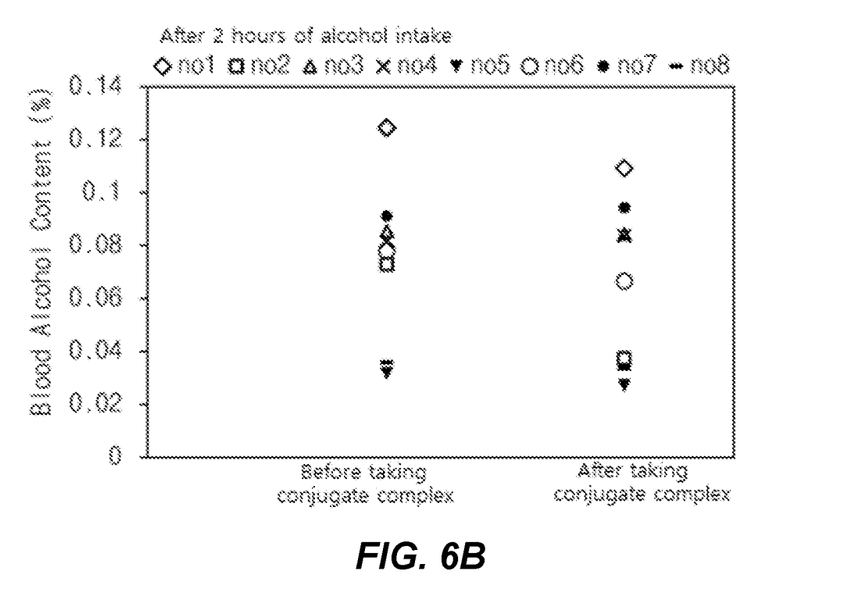

As a result, as illustrated in FIG. 6, it was confirmed that the group taking the conjugate complex of the present invention significantly lowered the blood alcohol concentration after 1 hour and 2 hours of alcohol intake, compared to a group in which only alcohol was taken (FIG. 6).

Therefore, from the above results, it can be seen that the conjugate of the sesamol and the peptide of the present invention induces rapid degradation of alcohol to relieve hangover.

The invention claimed is:

1. A pharmaceutical composition for preventing or relieving hangover comprising a conjugate of sesamol and a peptide as an active ingredient, wherein the peptide consists of an amino acid of SEQ ID NO: 1 or SEQ ID NO: 2.

2. The pharmaceutical composition for preventing or relieving hangover of claim 1, wherein the sesamol and the peptide are linked to each other by a linker.

3. The pharmaceutical composition for preventing or relieving hangover of claim 2, wherein the linker is dicarboxylic acid.

4. The pharmaceutical composition for preventing or relieving hangover of claim 1, wherein the composition increases the activity of alcohol dehydrogenase (ADH) or aldehyde dehydrogenase (ALDH).

5. The pharmaceutical composition for preventing or relieving hangover of claim 1, wherein the composition improves alcohol-induced motor impairment.

6. The pharmaceutical composition for preventing or relieving hangover of claim 1, wherein the composition has a formulation selected from the group consisting of powders, granules, tablets, capsules, suspensions, emulsions, syrups, external preparations, suppositories, and sterile injectable solutions.

7. A health food for preventing or relieving hangover comprising a conjugate of sesamol and a peptide as an active ingredient, wherein the peptide consists of an amino acid of SEQ ID NO: 1 or SEQ ID NO: 2.

8. The health food for preventing or relieving hangover of claim 7, wherein the conjugate is a conjugate of sesamol and a peptide consisting of an amino acid sequence of SEQ ID NO: 1, a conjugate of sesamol and a peptide consisting of an amino acid sequence of SEQ ID NO: 2, or a mixture thereof.

* * * * *

SEQUENCE LISTING

<160> NUMBER OF SEQ ID NOS: 8

<210> SEQ ID NO 1
<211> LENGTH: 9
<212> TYPE: PRT
<213> ORGANISM: Artificial Sequence
<220> FEATURE:
<223> OTHER INFORMATION: Peptide 1 for conjugation with sesamol

<400> SEQUENCE: 1

Ser Ile Pro Cys Lys Leu Gln Ser Gly
1               5

<210> SEQ ID NO 2
<211> LENGTH: 7
<212> TYPE: PRT
<213> ORGANISM: Artificial Sequence
<220> FEATURE:
<223> OTHER INFORMATION: Peptide 2 for conjugation with sesamol

<400> SEQUENCE: 2

Trp Leu Asn Arg Arg Ala Asn
1               5

<210> SEQ ID NO 3
<211> LENGTH: 20
<212> TYPE: DNA
<213> ORGANISM: Artificial Sequence
<220> FEATURE:
<223> OTHER INFORMATION: ADH4 forward primer

<400> SEQUENCE: 3
ctgaaaccat gaaagcagcc                                              20

<210> SEQ ID NO 4
<211> LENGTH: 21
<212> TYPE: DNA
<213> ORGANISM: Artificial Sequence
<220> FEATURE:
<223> OTHER INFORMATION: ADH4 reverse primer

<400> SEQUENCE: 4
gccgattatt agctcctctg g                                            21

<210> SEQ ID NO 5
<211> LENGTH: 20
<212> TYPE: DNA
<213> ORGANISM: Artificial Sequence
<220> FEATURE:
<223> OTHER INFORMATION: ALDH1 forward primer

<400> SEQUENCE: 5
ggagccaaaa gggtcatcat                                              20

<210> SEQ ID NO 6
<211> LENGTH: 20
<212> TYPE: DNA
<213> ORGANISM: Artificial Sequence
<220> FEATURE:
<223> OTHER INFORMATION: ALDH1 reverse primer

<400> SEQUENCE: 6
gtgatggcat ggactgtggt                                              20

<210> SEQ ID NO 7
<211> LENGTH: 23

```
<212> TYPE: DNA
<213> ORGANISM: Artificial Sequence
<220> FEATURE:
<223> OTHER INFORMATION: ALDH2 forward primer

<400> SEQUENCE: 7
caaattacag ggtcaactgc tat                                              23

<210> SEQ ID NO 8
<211> LENGTH: 22
<212> TYPE: DNA
<213> ORGANISM: Artificial Sequence
<220> FEATURE:
<223> OTHER INFORMATION: ALDH2 reverse primer

<400> SEQUENCE: 8
ccacactcac agttttcact tc                                               22
```